United States Patent [19]

O'Neil

[11] Patent Number: 4,583,410
[45] Date of Patent: Apr. 22, 1986

[54] TIMING CIRCUIT FOR ACOUSTIC FLOW METERS

[75] Inventor: Jeffrey C. O'Neil, Tulsa, Okla.

[73] Assignee: Nusonics, Inc., Tulsa, Okla.

[21] Appl. No.: 614,566

[22] Filed: May 29, 1984

[51] Int. Cl.⁴ .............................................. G01F 1/66
[52] U.S. Cl. .................................... 73/861.28; 73/597
[58] Field of Search ........... 73/861.27, 861.28, 861.29, 73/861.31, 597

[56] References Cited

U.S. PATENT DOCUMENTS

| 3,869,915 | 3/1975  | Baumoel       | 73/861.28 |
| 3,918,304 | 11/1975 | Abruzzo et al.| 73/861.29 |
| 4,028,938 | 6/1977  | Eck           | 73/861.31 |
| 4,232,548 | 11/1980 | Baumoel       | 73/861.28 |
| 4,425,805 | 1/1984  | Ogura et al.  | 73/861.29 |

Primary Examiner—Charles A. Ruehl
Attorney, Agent, or Firm—Head, Johnson & Stevenson

[57] ABSTRACT

A timing means for determining the time of travel of ultrasonic pulses between a transmitter and a receiver immersed in a fluid. The first time instant is determined when the transmitter transmits an ultrasonic pulse in the fluid. A second time instant is determined when the ultrasonic wavelet has been detected, converted to electrical signal, and the zero crossing time of the electrical wavelet after a selected positive peak is determined. Timing means are provided to determine the time interval between the first and second time instants. This is done by having a coarse time clock and counter. The number of full clock periods before the second instant is determined, and a ramp of voltage is generated having a known rate of rise. The ramp is negatively biased and the bias voltage is varied until the ramp voltage reaches zero at the second instant. The transmitter upstream is fired, and the wavelet is detected at the downstream transducer. Simultaneously, or sequentially the downstream transducer is powered to generate a wavelet and the second wavelet is detected at the upstream transducer. The rate of flow of the fluid is a function of the difference between these two time intervals.

11 Claims, 6 Drawing Figures

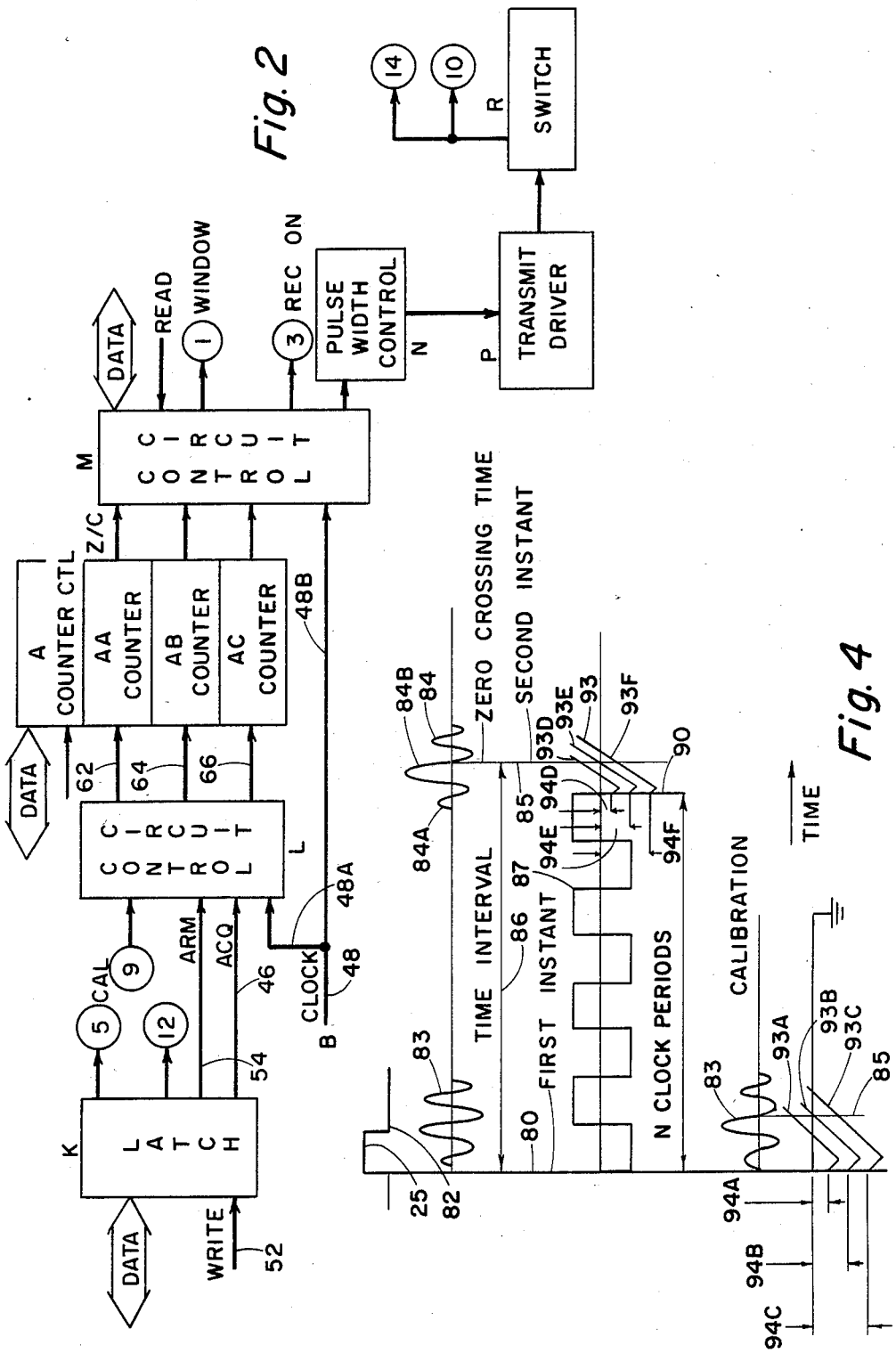

TIMING CIRCUIT FOR ACOUSTIC FLOW METERS

BACKGROUND OF THE INVENTION

1. Field of the Invention

This invention relates to the field of ultrasonic flow meters, for determining the rate of flow of a fluid in a conduit. More particularly, this invention is related to means and method for determining the flow rate more precisely than has been possible in the past.

2. Description of the Prior Art

A convenient and commonly used means of measuring fluid flow is by the use of sonic flow meters. These are devices which transmit sound pulses or wavelets through the fluid flowing in a conduit. In the most commonly practiced means of employing ultrasonics for measuring fluid flow rate, an ultrasonic path is provided between an upstream and downstream location, spaced on opposite sides of a conduit. The rate of travel of the sound through the liquid is measured in both directions, that is, with the liquid flow direction against the sonic flow, and the other direction where the liquid flow direction and the sonic flow direction are the same. In the preferred method for practicing the invention, the rate of travel of the sound through the liquid is measured in both directions, that is, with the fluid component direction with and against the fluid flow component. By subtracting such measurements which effectively cancels out the rate of sound flow upon travel through the fluid itself, the rate of fluid flow can be accurately determined.

There have been a number of prior art patents describing such systems, mainly with the point of view of correcting for temperature or viscosity or other variables which would affect the precision of the measurement.

In this invention the emphasis is placed on the method of measuring time intervals precisely, so that the most accurate value of velocity can be determined.

SUMMARY OF THE INVENTION

It is a primary object of this invention to provide a more precise method for determining the rate of flow of a fluid in a conduit.

It is a further object of this invention to make this precise measurement by determining a first time instant when an ultrasonic wavelet is transmitted from a first transducer and is received at a second transducer spaced a known distance in the fluid. The instant of reception or detection is learned by determining the first full positive cycle peak in the received wavelet and then determining the instant of zero crossing of that positive wavelet. The time interval is then determined between the first instant of transmitting the wavelet and the second instant of determination of the zero crossing after the first peak.

It is a still further object to provide a means of measuring the length of this time interval between the first and second instants by using a coarse clock period to determine the end of the last complete clock period before the second instant, and creating a ramp voltage of known rate of rise, and determining the time instant when the zero crossing voltage intersects the ramp and determining the total time.

Before explaining in detail the present invention, it is to be understood that the invention is not limited in its application to details of the construction and arrangement of parts illustrated in the accompanying drawings. The invention is capable of other embodiments and of being practiced or carried out in a variety of ways. It is to be understood that the phraseology and terminology employed herein is for the purpose of description and not of limitation.

Also, although this method can be carried out in both liquids and in gases, it will, for convenience, and not by way of limitations, be described in terms of liquid flow.

Also, it will be described in terms of positioning the transducers on opposite sides of the liquid flow conduit, one downstream from the other, as shown in FIG. 5, rather than being placed colinearly in the liquid flow.

In a liquid flow conduit, two ultrasonic transducers are positioned on opposite sides of the conduit, one downstream from the other and they are directed along a line from a first to a second transducer. Means are provided for generating a starting time pulse at the beginning of a clock period and generating an ultrasonic wavelet in the liquid surrounding the transducer in the pipe or conduit. This ultrasonic pulse will be a multicycle oscillation due to the characteristics of the transducer, and this oscillatory short pulse will travel through the liquid in the pipe to a second transducer and will generate a corresponding electrical signal having substantially the same wave shape. The presence of an Nth positive peak of sufficient amplitude is determined and the following zero crossing is determined by a comparator. A clock is provided of known frequency and period, and means are provided for determining the total N of complete clock periods within the time interval between the first and second instants. At the end of the Nth clock period, a ramp voltage is generated biased below zero, and the time instant at which this ramp voltage reaches zero potential is determined. If this instant is earlier or later than the zero crossing time, the bias voltage of the ramp voltage is varied until the point of zero volts on the ramp is precisely the same instant as the zero crossing of the received signal. From the known rate of rise of the ramp voltage and the bias voltage below the ground and the number of full clock periods, the time interval between the transmission and reception can be determined.

Means are provided to calibrate the instrument by placing a starting pulse at the input to the signal amplifier following the receive transducer, and determining the precise time interval until that signal is received in relation to the zero crossing time. This provides a measure of the difference in time between the transmit pulse and the received wavelet. The time to the zero crossing point is, of course, longer than the arrival time of the wavelet, but since the arrival time is a very difficult thing to measure, a more dependable time is developed by the zero crossing method and this delay between the reception of the beginning of the wavelet and the zero crossing time can be determined as a correction to the total flow time.

There are four principal components to this instrument. One is a control and power supply means which can generate the transmitter voltages. There are two identical receiver systems which accept the received pulse at the second transducer and make the determination of second time instant, and determine the time interval between the first and second time instants. There is a fourth unit which is a microprocessor which controls the timing of all actions, and the flow of all data.

BRIEF DESCRIPTION OF THE DRAWINGS

These and other objects and advantages of this invention and a better understanding of the principles and details of this invention will be evident from the following description, taken in conjunction with the appended drawings, in which:

FIG. 2 is a schematic diagram of one of the receive signal processing systems. There are two of these in a complete unit.

FIG. 4 indicates schematically the relative time intervals which are involved in this invention.

DESCRIPTION OF THE PREFERRED EMBODIMENT

Figure 5:
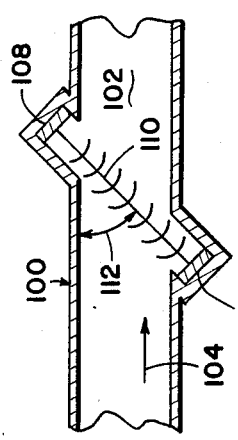
FIGS. 5 and 6 illustrate two prior art arrangements of transducers with reference to the liquid flow conduit.

Referring now to the drawings and in particular to FIG. 5 there is a schematic diagram of the prior art arrangement of two ultrasonic transducers 106 and 108 mounted in the opposite walls of a pipe or conduit 100 through which a fluid 102 is flowing in the direction of the arrow 104.

Figure 1:
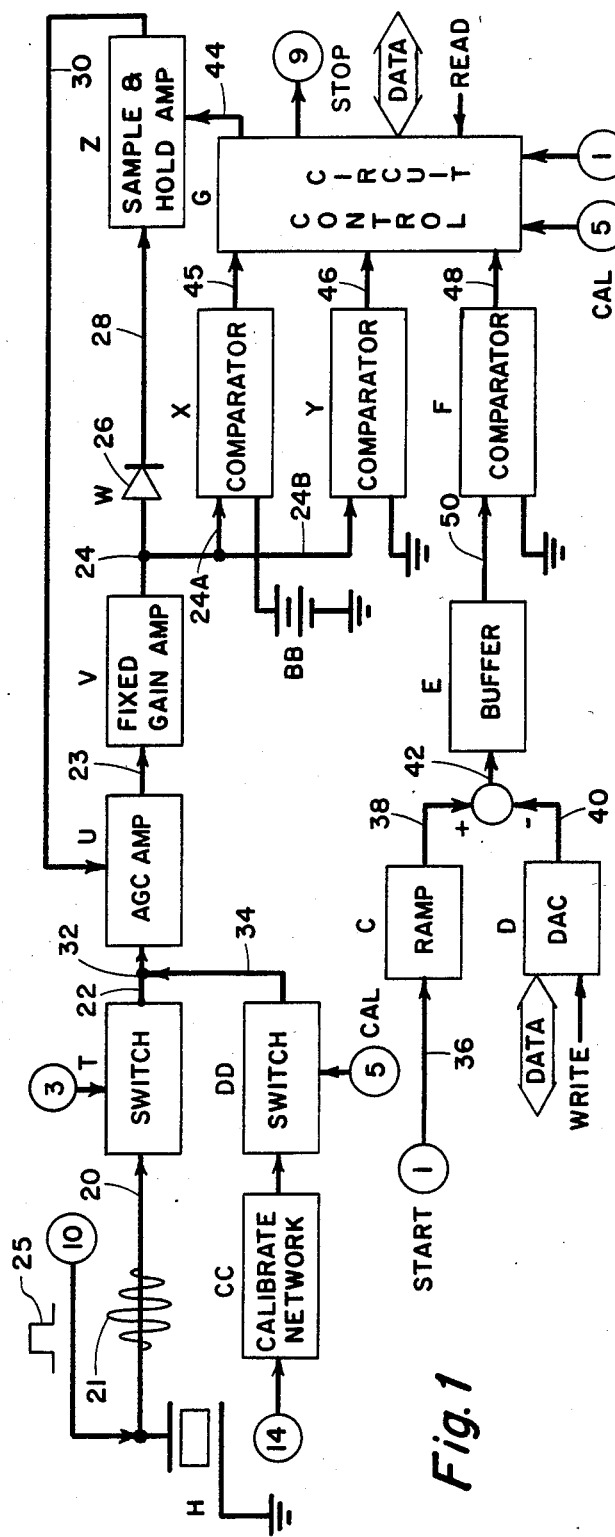
FIG. 1 is a schematic diagram of the control and power supply unit.

Referring now to FIGS. 1 and 2 there is shown schematically a preferred embodiment of this invention. FIG. 2 represents schematically the control and power supply portion of the equipment and FIG. 1 represents schematically the circuit diagram of the receiving or detecting apparatus, and the time measuring apparatus of this invention. There are two complete units corresponding to FIG. 2 so that an ultrasonic wavelet can be transmitted from an upstream transmitter to a downstream receiver transducer, while simultaneously, or sequentially, an ultrasonic signal can be transmitted from the downstream transducer to the upstream transducer. Both of these operations are required to make a determination of the rate of flow of fluid in the pipe or conduit of FIG. 4.

In FIG. 1 there is one transducer H shown with one terminal grounded and the other terminal supplied by voltage 10 from the switch R of FIG. 2. The switch R is driven by a pulse width control N that receives power from the control circuit M. This pulse is amplified by the transmit driver P, which controls the switch R to provide and driving voltage to the terminal 10 of FIG. 1.

At a short time later the switch T is supplied with a signal 3 from FIG. 2 which enables the receiver, so as to pass the voltage from the receiver transducer H which is transmitted by line 20 from the transducer H to the switch T, and then passed on by lead 22 to an AGC, or automatic gain control amplifier U. The purpose of the AGC amplifier is to output a signal on line 23 to a fixed gain amplifier V then to the sample and hold amplifier Z. The output of the sample and hold amplifier goes by way of lead 30 back to the AGC amplifier so as to control the output of the AGC amplifier on line 24 to a selected value. The pulse 25 shows the nature of the signal provided to terminal 10 to transmit an ultrasonic wavelet from the transducer H. The oscillatory wavelet 21 represents the electrical wavelet generated by the transducer H when the signal put out by the opposite transducer of the nature of 25 reaches the receiving transducer. The wavelet 21 passes through the switch T and through the AGC amplifier U and the fixed amplifier V to a diode W which passes the peak voltage of the separate pulses or peaks of the ultrasonic wavelet 21. This peak wavelet at point 24 is transmitted over line 24A to a comparator X which compares the voltage on line 24A with the voltage BB of a battery which represents the comparison voltage. So long as the voltage 24A is of the order of magnitude of voltage BB, the AGC amplifier and so on, are operating properly.

Turning momentarily to FIG. 4, there is shown a wavelet 83 which is the output of the transmitting transducer and the corresponding wavelet 84 is the electrical signal supplied by the receiving transducer. The AGC amplifier is required in order to be assured that the Nth (or second) peak 84B, for example, is of sufficient size as compared to the first peak so that it is definitely above the noise, and represents true signal transmitted from the transducer. That fact is proven by the comparator X which says that the peak is large enough to be a true signal. That information goes by lead 45 to the control circuit G.

The next point is to determine the timing instant of the zero crossing of the first large peak of the signal 84B. This zero crossing time 85 is shown, and is what will be called the second instant. The first instant of time is represented by the line 80 which is, for example, the time when the transmitter is powered by the voltage from 10 by the pulse 25, and the ultrasonic wavelet 83 is initiated in the fluid within the pipe. Further as in FIG. 4, the time interval 86 between the first instant of time 80 and the second instant of time 85 is the actual travel time of the wavelet from the transmitter to the receiving transducer.

In FIG. 2 there is a clock B which puts out a timing signal of constant frequency. This signal is provided over lines 48 and 48A to the control circuit L and over the line 48B to the control circuit M. This is shown in FIG. 4 as the square wave 87. When a number N of complete clock periods is completed, (with less than another clock period available to the second time instant), at the end of the Nth clock period, which in the case illustrated, is the fourth clock period, there is a ramp voltage generated as in box C of FIG. 1. This is a voltage which starts at zero (ground), drops negative, then increases in positive value with time at a uniform known rate. The box D is a digital-to-analog converter DAC which receives over the data line from the control computer or microprocessor, a digital number of the order of say 800. This can be any value within the range of the DAC, but the number is a measure of the bias of the ramp voltage below zero. This bias voltage of D on line 40 is added to the ramp voltage 38 from C and these together on line 42 go to a buffer and on line 50 to a comparator F. The comparison voltage (is zero) or ground, and when the voltage on line 50 passes through zero, going positive, this instant of time is coincident with the second instant line 85. Shown in FIG. 4 is the last cycle 87 of the clock B and the beginning of the ramp voltage. In other words, when the last of N clock cycles occurs at line 90, control circuit M generates a signal through lead 1, FIG. 1, to line 36, which starts the ramp signal 93.

The bias voltages 94D, 94E, 94F, represent the amount of voltage below ground that this ramp is biased. The value of bias voltage is varied until the ramp such as 93E crosses the zero line at the same time that the zero crossing 85 of the wavelet 84 occurs. In that case the time from first instant 80 to second instant 85 would be represented by N clock periods and the time from the start of the ramp line 90 to the zero crossing line 93E. The magnitude of the bias voltage line 94E is related to this smaller time interval, line 90 to line 93E.

If, on the other hand, the value of 85 occurred earlier, then the computer would send a signal to decrease the bias voltage which would shift the point of zero crossing of the ramp earlier until it occurred at the same time that the zero crossing of the received wavelet occurred. When that happens, the comparator F will show that the value of bias of the ramp voltage is correct and that then is communicated to the control circuit G over line 48.

By trial and error the bias voltage is determined such that the ramp voltage reaches zero at the same time instant that the zero crossing of the receive signal reaches zero and that bias voltage is now a measure of the time between the end of the last full period 87 or time line 90 or bias voltage 94D and when combined with the known time of N clock periods from line 80 to line 90, that is the answer that is required as the measure of the time interval between the first instant and the second instant.

The ramp voltage is of sufficient range in time and voltage that it can delineate a time interval of the order of 900 nano seconds. Thus, it is not required to have the last complete cross-over of the time clock zero crossing since the 900 nano seconds represent something over two full periods of the clock.

In FIG. 4 there is shown a wavelet 83 which represents the transmitted wavelet within the liquid at the position of the transmitting transducer, and the wavelet 84 represents the same wavelet even though it may be changed somewhat by transmission, at the position of the receiving transducer.

Referring again to FIGS. 2 and 4, there is a box CC which is a calibration network and it gets a pulse at the same time that the transmitting transducer receives the pulse which generates the wavelet. The switch DD is controlled by a calibrate signal 5 which comes from the latch K of FIG. 2. When the calibration pulse 83 is generated, the starting point is, of course, the time 80 when the first voltage pulse is first applied to the transmitting transducer. That signal 83 is applied over the line 34 to the intersection 32 and the AGC amplifier U. The AGC amplifier and the following apparatus is not aware that this is a calibration signal or an actual received signal and it proceeds to measure the time between the initiation of the wavelet 83 and the zero crossing of the first large positive pulse 84B.

In this case, the clock is started in advance of line 80 and the bias voltage is set such that the ramp crosses through zero volts at the same time as the zero crossing of the wavelet 83.

Again, the bias voltages and the number of clock cycles the ramp was started prior to the line 80 are a measure of that time delay and will be a precise measurement of the time between the start of the ultrasonic oscillatory pulse and the time of the zero crossing. This magnitude of time can be subtracted from the timed interval 86 of FIG. 4 to set ahead the point of detection of the position of the received signal so that the precise time interval between the initiation voltage and the receive voltage can be determined.

Figure 3:
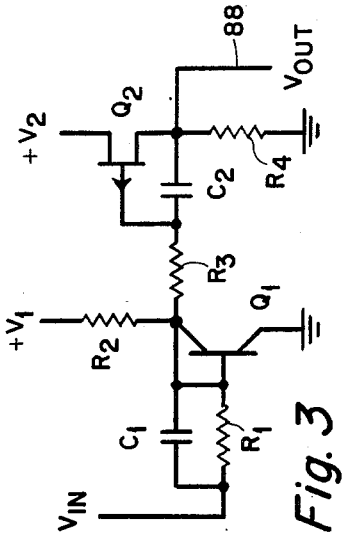
FIG. 3 is a schematic diagram of one type of ramp generator circuit.

In FIG. 3 is shown a schematic diagram of voltages, resistors and capacitors in combination with a transistor Q1 and a mossfet Q2 whereby the voltage output from the junction between capacitor C2 and resistor R4 would be a ramp voltage which starts from a desired negative voltage, drops down on a decreasing ramp and then starts an increasing ramp. The MOS field effect transistor Q2 provides a uniformly increasing voltage through resistor R4 to provide the ramp voltage.

Figure 6:
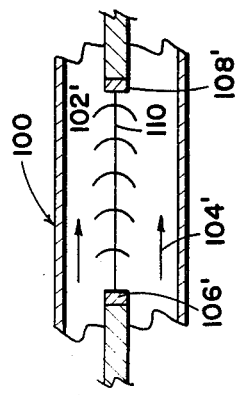

Referring to FIG. 6, there is shown another prior art arrangement of transducers in a flowing fluid in a pipe or conduit Here the line 110 joining the transducers 106' and 108' is parallel to the direction of flow of the fluid, as shown by the arrow 104'. For the geometry shown in FIG. 6, the flow rate of fluid=F $$F = K(1/TD - 1/TU),$$

where
K = a determinable constant for a particular geometry
TD = time interval for transmission downstream
TU = time interval for transmission downstream For the case of FIG. 5, the algebra is the same but because of the different geometry account must be taken of the component of the TD and TU in the direction of fluid flow, that is, because of angle 112 of FIG. 5.

What has been described is an improved method of determining the precise time of travel of the wavelet from a transmitting transducer initiated at a first instant of time until it is received at a second transducer and has developed a pre-selected magnitude of voltage which represents the second instant of time. Also shown and described is a preferred method of determining the precise time interval between the first and second time instants. Also, as been shown, a method of determining the delay in the received signal or the delay of the second time instant after the initiation of the transmitted wavelet before the counting of time is stopped. Thus, the time of transmission can be calculated precisely from a selected point on the transmitted wavelet to a corresponding selected point on the received wavelet. This method of measurement involves as has been stated, determination of a number M of complete clock periods plus the time between the initiation of a negatively biased increasing ramp voltage, to the time that it reaches a value of ground potential at the same instant that the received signal is detected.

It is, of course, possible also to provide a clock of very high frequency and a counter that is also of very high frequency so that if the period of the clock is comparable to the precision of determination of time intervals, the number of counts of the counter between the first time instant and the second time instant will provide this information.

While the invention has been described with a certain degree of particularity, it is manifest that many changes may be made in the details of construction and the arrangement of components without departing from the spirit and scope of this disclosure. It is understood that the invention is not limited to the exemplified embodiments set forth herein but is to be limited only by the scope of the attached claim or claims, including the full range of equivalency to which each element thereof is entitled.

What is claimed is:

1. The method of measuring the time of travel of a first wavelet of ultrasonic energy in a liquid from the first time instant of generating said first wavelet by a first transducer at a first point until the reception of said first wavelet by a second transducer at a second spaced point in said liquid, comprising:

(a) transmitting said first wavelet of ultrasonic energy at said first instant of time from said first transducer to a second transducer positioned at a second spaced point in said liquid;

(b) detecting the arrival of said wavelet of ultrasonic energy at said second transducer, and producing a corresponding electrical signal wavelet;

(c) amplifying said electrical signal wavelet until a selected peak in said wavelet of electrical signal is a selected magnitude;

(d) determining a second time instant of the first zero crossing after said selected peak;

(e) producing a sequence of clock pulses;

(f) starting a pulse counter to count said clock pulses at said first instant of time, and stopping said counter at the completion of the last full period of a clock pulse before said second instant;

(g) starting a ramp voltage of known rate of rise at the end of the last full period of the clock pulse before said second instant; and (h) comparing said ramp voltage with a selected reference voltage whereby from the known rate of rise of said ramp voltage and said count of said clock pulses the time interval between said first and second instants of time can be determined.

2. The method as in claim 1, in which said first and second transducers are positioned in opposite walls of a conduit carrying a flowing selected liquid and said first transducer is upstream of said second transducer.

3. The method as in claim 1 in which said first and second transducers are positioned in opposite walls of a conduit carrying a flowing selected liquid and said first transducer is downstream of said second transducer.

4. The method as in claim 1, in which said first and second transducers are positioned in a conduit carrying a flowing selected liquid; with the line joining them parallel to the direction of flow of said liquid and said first transducer is upstream of said second transducer.

5. The method as in claim 1, in which said first and second transducers are positioned in a conduit carrying a flowing selected liquid with the line joining them parallel to the direction of flow of said liquid; and said first transducer is downstream of said second transducer.

6. The method as in claim 1 in which the improvement in said method comprises the additional steps of:

(i) carrying out steps (a) through (h) with the first transducer upstream from said second transducer, and determining a first time interval between said first and second instants of time;

(j) carrying out steps (a) through (h) with the first transducer downstream from said second transducer; and determining a second time interval between a third and a fourth instant of time; and (k) utilizing said two time intervals and the spacing between said transducers for determining the rate of flow of said liquid.

7. The method as in claim 6 in which the steps (i) and (j) are carried out sequentially.

8. The method as in claim 6 in which the steps (i) and (j) are carried out simultaneously.

9. The method as in claim 1 in which said wavelet of ultrasonic energy comprises a multi-cycle wavelet, with one peak higher than the others.

10. The method as in claim 1 in which said wavelet of ultrasonic energy is a multi-cycle wavelet and said second instant is the time of zero crossing of said electrical signal wavelet after the Nth peak of the electrical signal wavelet.

11. Apparatus for measuring the time of travel of a first wavelet of ultrasonic energy in a liquid from the first instant of generating said first wavelet by a first transducer at a first point until the reception of said first wavelet by a second transducer at a spaced second point, comprising:

(a) a first and a second ultrasonic wavelet transducer means positioned in said liquid at a first and second point respectively, each transducers being adapted to sequentially transmit or to detect ultrasonic wavelets in said liquid;

(b) means to apply transmitting power at a first time instant to said first transducers said second transducer being adapted to detect said ultrasonic signal and to generate a corresponding electrical signal;

(c) means to determine a second time instant which occurs at the zero crossing of said electrical signal following a selected peak of said electrical signal;

(d) clock means, the known period of which is large compared to the desired precision of measurement of said time of travel;

(e) means for starting a pulse counter responsive to said clock means at said first instant and for determining the maximum number N of complete clock periods before said second instant;

(f) means to start at the end of said N clock periods a ramp voltage of known rate of rise and determining the value of said ramp voltage at said second instant whereby, from the known rate of rise of said ramp voltage the known clock period and the number N, the time of travel can be determined.

* * * * *